(12) United States Patent
Thorson

(10) Patent No.: US 8,695,402 B2
(45) Date of Patent: Apr. 15, 2014

(54) INTEGRATED IR SOURCE AND ACOUSTIC DETECTOR FOR PHOTOACOUSTIC GAS SENSOR

(75) Inventor: Walter Thorson, Calgary (CA)

(73) Assignee: Honeywell International Inc., Morristown, NJ (US)

( * ) Notice: Subject to any disclaimer, the term of this patent is extended or adjusted under 35 U.S.C. 154(b) by 528 days.

(21) Appl. No.: 12/792,822

(22) Filed: Jun. 3, 2010

(65) Prior Publication Data

US 2011/0296900 A1    Dec. 8, 2011

(51) Int. Cl.
*G01N 29/02*    (2006.01)
*G01N 21/17*    (2006.01)

(52) U.S. Cl.
USPC ............................................. 73/24.02

(58) Field of Classification Search
USPC ............................................. 73/24.02
See application file for complete search history.

(56) References Cited

U.S. PATENT DOCUMENTS

| | | | | |
|---|---|---|---|---|
| 4,622,845 A | * | 11/1986 | Ryan et al. | 73/24.02 |
| 5,129,262 A | * | 7/1992 | White et al. | 73/599 |
| 5,189,914 A | * | 3/1993 | White et al. | 73/599 |
| 5,310,610 A | * | 5/1994 | Furubayashi et al. | 430/11 |
| 5,616,826 A | * | 4/1997 | Pellaux et al. | 73/24.02 |
| 5,721,430 A | * | 2/1998 | Wong | 250/339.13 |
| 5,753,797 A | * | 5/1998 | Forster et al. | 73/24.01 |
| 5,869,749 A | * | 2/1999 | Bonne et al. | 73/53.01 |
| 5,886,249 A | * | 3/1999 | Bonne et al. | 73/24.02 |
| 6,006,585 A | * | 12/1999 | Forster | 73/24.01 |
| 6,076,392 A | * | 6/2000 | Drzewiecki | 73/23.2 |
| 6,082,178 A | * | 7/2000 | Bernstein et al. | 73/24.02 |
| 6,222,190 B1 | * | 4/2001 | Bernstein et al. | 250/343 |
| 6,239,436 B1 | * | 5/2001 | Parker et al. | 250/341.8 |
| 6,344,647 B1 | | 2/2002 | Jourdain et al. | 250/339.07 |
| 6,373,056 B1 | | 4/2002 | Johnson et al. | 250/339.13 |
| 7,091,869 B2 | * | 8/2006 | Forster et al. | 340/628 |
| 7,187,961 B2 | * | 3/2007 | Yamashita et al. | 600/310 |
| 7,213,444 B2 | * | 5/2007 | Baraket et al. | 73/24.01 |
| 7,304,732 B1 | * | 12/2007 | Polcawich et al. | 356/246 |

(Continued)

FOREIGN PATENT DOCUMENTS

FR    2 791 134    9/2000
JP    2002-328116    11/2002

OTHER PUBLICATIONS

"Transistor Case Packages: TO-39 Metal Can," Nov. 2013, www.interfacebus.com, 3 pages.*

(Continued)

*Primary Examiner* — John Fitzgerald
(74) *Attorney, Agent, or Firm* — Husch Blackwell LLP

(57) ABSTRACT

A photoacoustic gas detector includes an integrated source, infrared filter and an acoustic sensor. The source, filter and acoustic sensor can be integrated onto one or more semiconductor substrates, such as silicon. Processing circuitry can also be integrated onto the substrate. Further, the source, filter and acoustic sensor can be integrated into a single component package, such as a metal can transistor package.

11 Claims, 3 Drawing Sheets

(56) References Cited

U.S. PATENT DOCUMENTS

| | | | |
|---|---|---|---|
| 7,827,851 B2 * | 11/2010 | Lee | 73/31.05 |
| 7,895,880 B2 * | 3/2011 | Fritz et al. | 73/24.02 |
| 7,896,053 B2 * | 3/2011 | Simandl et al. | 156/753 |
| 7,936,062 B2 * | 5/2011 | Humpston et al. | 257/704 |
| 8,359,904 B2 * | 1/2013 | Nicoletti et al. | 73/24.02 |
| 2003/0112019 A1 * | 6/2003 | Forster et al. | 324/633 |
| 2003/0190262 A1 * | 10/2003 | Blazewicz et al. | 422/94 |
| 2004/0000713 A1 * | 1/2004 | Yamashita et al. | 257/728 |
| 2006/0009707 A1 * | 1/2006 | Daniels et al. | 600/532 |
| 2007/0190747 A1 * | 8/2007 | Humpston et al. | 438/460 |
| 2009/0320561 A1 * | 12/2009 | Fritz et al. | 73/24.02 |
| 2011/0088453 A1 * | 4/2011 | Nicoletti et al. | 73/24.02 |
| 2011/0290002 A1 * | 12/2011 | Heidrich et al. | 73/24.02 |

OTHER PUBLICATIONS

"Transistor Package Style: TO-8 Metal Can," Nov. 2013, www.interfacebus.com, 2 pages.*

European Search Report corresponding to Application No. EP 11 16 7903, dated Jan. 28, 2012.

English translation of abstract of French Publication No. FR 2791134 (A1).

English translation of abstract of Japanese Publication No. 2002328116.

* cited by examiner

INTEGRATED IR SOURCE AND ACOUSTIC DETECTOR FOR PHOTOACOUSTIC GAS SENSOR

FIELD

The invention pertains to photo-acoustic gas detectors. More particularly, the invention pertains to such detectors which include integrated packaging of an infrared source and an acoustic detector.

BACKGROUND

In recent years, photo-acoustic gas sensors have emerged as a viable technology for a number of gas sensing applications, including CO2 monitoring for Indoor Air Quality and Demand Control Ventilation, Refrigerant and Ammonia monitoring, and flammable gas detection, among others. Photoacoustic technology is similar in many respects to Non-Dispersive Infra-Red (NDIR) and other spectroscopic means of gas detection. All of these techniques exploit the selective absorption of infra-red radiation by the gas sample to determine the concentration or composition of the sample.

The photoacoustic sensing technique does not rely on direct measurement of the amount of IR radiation passing through the gas sample, but instead detects the resulting expansion of the gas sample as input IR radiation is absorbed by the gas. If the input radiation is sinusoidally modulated at acoustic frequencies, the resulting expansion of the gas can be detected as an acoustic waveform using low cost detection means such as a MEMS microphone. Generally, practical photoacoustic gas sensors can be realized with much smaller gas sensing chambers compared with traditional NDIR gas sensors because they are much less dependent on optical path length within the sensing chamber to achieve useful detection sensitivities. This difference allows the possibility to realize miniaturized gas sensors in a tightly integrated package using microelectronics and MEMS fabrication techniques. It is desirable to improve sensor performance, reliability and cost while reducing sensor package size and manufacturing requirements.

The functional principle of photoacoustic gas sensing is well known in the art. The required functional elements of the sensor include an infrared source, an optical wavelength selective filter, a gas sensing volume (detection chamber), a gas permeable membrane or valve that permits gas to diffuse freely into the detection chamber but restricts bulk flow out of the chamber when the gas is expanding, a measurement microphone or other suitable pressure transducer, and a control and signal processing means to modulate the IR source and acquire and process the photoacoustic signal and output the resulting measurement.

Photoacoustic sensors may also include structures for compensating or canceling the effects of ambient noise and pressure variation on the sensor. This can be accomplished using a separate reference sensing volume and reference microphone to obtain a background noise signal that is substantially free of a photoacoustic component from the gas of interest. This background signal is subtracted from the signal detected within the gas sensing volume to generate a photoacoustic signal that is substantially free from background noise effects, thereby improving sensor accuracy.

FIG. 1 illustrates a known arrangement of sensor components to demonstrate the functional principle of photoacoustic gas detection. Certain aspects of the sensor physical design not critical to describing the general functional principle have been omitted for clarity. Within the photoacoustic gas sensor 1, modulated infrared light emitted by a infrared source 2 is directed by means of a reflector housing 3 through a wavelength selective bandpass IR filter 4 into the gas sensing volume 5, the volume of which is defined by measurement cell body 6 and the IR filter 4.

Gas from the ambient atmosphere 7 readily diffuses through a gas permeable membrane 8 and apertures 9 in the measurement cell body thereby entering the gas sensing volume 5. A portion of the modulated IR irradiation is absorbed by the target gas to be detected within the sensing volume giving rise to a modulated acoustic pressure wave which is detected by means of a microphone 10 that is communicatively coupled with the measurement cell volume through an opening 11 in the measurement cell body.

With appropriate selection of the IR source, filter and microphone characteristics, the magnitude of the acoustic pressure wave will be directly related to the concentration of the target gas of interest. In this illustrative example, the components of the microphone and the filament lamp IR source are disposed upon a shared printed circuit board 12 which could also include the associated lamp modulation and processing electronics circuitry (not shown for clarity).

DETAILED DESCRIPTION

Figure 1:
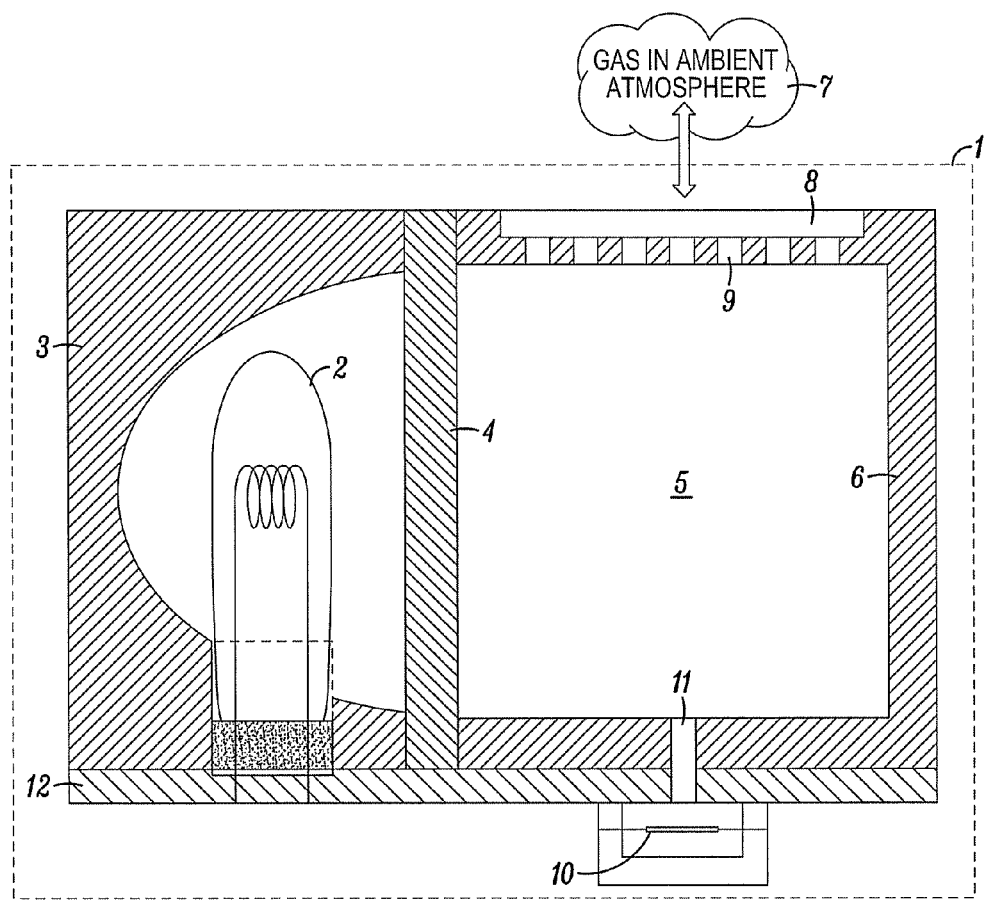
FIG. 1 illustrates the functional principle of a photoacoustic gas sensor.

While embodiments of this invention can take many different forms, a specific embodiment thereof is shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the invention integrate core photoacoustic sensor functional elements into a single, integrated MEMS device suitable for mass production. These embodiments provide the advantages of robustness and low cost as afforded by MEMS technology. In one aspect of the invention, an integrated IR source, fixed wavelength IR filter and a MEMS microphone can be integrated in a single component package and fitted to a gas measurement cell.

Figure 2A:
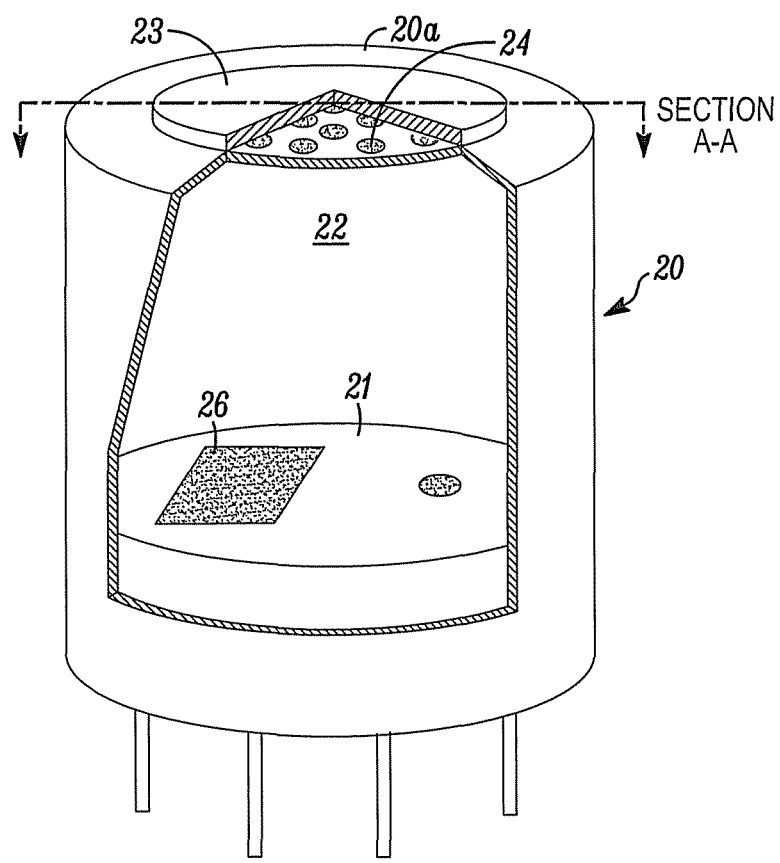
FIGS. 2A, 2B depict a first embodiment of a photoacoustic gas sensor according to the present invention.
Figure 2B:
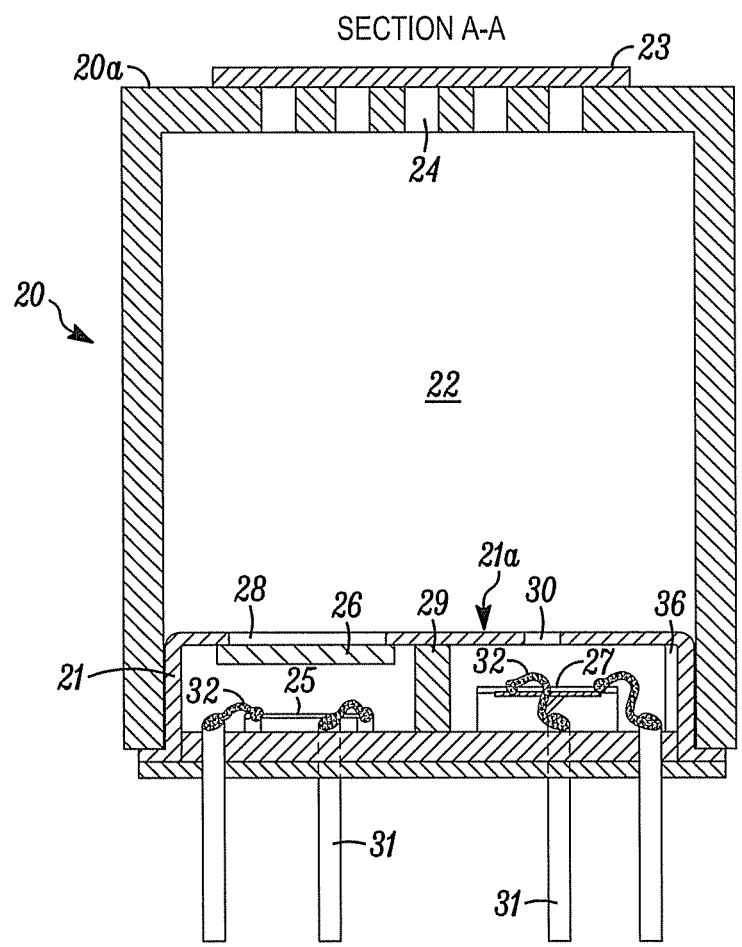

FIGS. 2A and 2B depict an embodiment of the invention where a number of the functional elements described in FIG. 1 have been consolidated into an integrated component that may be fabricated using MEMS and microelectronics packaging techniques. FIG. 2A is a partial cutaway perspective view of the invention, and FIG. 2B is a cross-section side view of the invention in the plane of section A-A as shown in FIG. 2A.

In this embodiment of the invention, an injection molded plastic measurement cell body 20 is bonded to an integrated IR source and microphone component body, or package, 21 packaged in the format of an hermetically sealed metal can component package of the type commonly used to package transistors and other electronics components. This type of electronics component packaging is commonly referred to as a "transistor can package or TO can" and typically conforms to dimensions described in electronics industry norms published by JEDEC and the Electronics Industry Association.

These packages are available in a number of standard sizes and interconnect pin configurations to suit the needs of the particular application. Standard package sizes such as JEDEC TO39 or TO8 cans are exemplary of preferred packages sizes that could be used for this invention. The interior surface of the measurement cell body 20 is plated with an IR reflective material (for example, but without limitation, gold plating) to maximize the IR energy that is directed into the gas within the measurement cell volume 22, that is formed by the joining together of the measurement cell body 20 and the integrated component package 21.

A gas permeable membrane 23 is bonded to an outer surface 20a of the measurement cell body 20 using adhesive or other suitable means. A plurality of holes 24 in the measurement cell body are located beneath the gas permeable membrane 23 and provide flow paths for gas from the ambient atmosphere to diffuse into and out of the measurement cell volume 22. The integrated component comprises a planar infrared source 25, a wavelength selective filter 26, and a MEMS-type microphone 27. The IR filter covers an opening 28 in the component package 21 providing a window through which IR energy of the selected wavelength may radiate into the measurement cell volume 22.

An internal baffle structure 29 within the integrated component package 21 prevents radiation from the IR source from coupling directly to the MEMS microphone inside the shared TO can package 21. The baffle also provides for the portion of the integrated component containing the IR source to be sealed under vacuum during component assembly.

The photoacoustic signal generated within the gas measurement volume is communicatively coupled to the MEMS microphone through an opening 30 in the top face of the integrated component package. The IR source and the MEMS microphone are connected to external leads 31 of the integrated component using a plurality of wire bonds 32 of the type normally used in microelectronics and semiconductor packages.

Processing circuitry 36 could also be included within the integrated component package 21 to acquire and process signals from the microphone 27. It will be understood that the circuitry 36 could be formed on a semiconductor substrate in the package 21. This substrate could be the same substrate that supports the microphone 27, or it could be different.

In one aspect of the invention, the fabrication of both the IR source and detection element could be implemented in a single integrated component and incorporated into a photoacoustic gas detector. Signal processing electronics could also be realized on the same die or within the same TO can package, leading to a single chip or single component solution for all active components of a photo-acoustic gas detector. Such integration could be expected to provide reliability and performance improvements as well as manufacturing and cost efficiencies relative to prior art implementations.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A photoacoustic gas sensor component comprising:
an infrared source;
an integrated microphone;
an infrared wavelength selective bandpass filter, wherein the infrared source, the integrated microphone, and the infrared wavelength selective bandpass filter are integrated into a single hermetically sealed package;
an internal baffle structure within the hermetically sealed package that prevents radiation from the infrared source from coupling directly to the integrated microphone; and
a gas measurement cell fitted on a single end of the hermetically sealed package wherein the infrared wavelength selective bandpass filter forms a window between a gas measurement volume of the gas measurement cell and the infrared source within the hermetically sealed package and wherein the gas measurement volume is communicatively coupled to the integrated microphone though an opening in a face of the hermetically sealed package.

2. The photoacoustic gas sensor component as in claim 1 where the microphone is implemented as a MEMS-type transducer.

3. The photoacoustic gas sensor component of claim 1 where the single hermetically sealed package includes a TO39 or TO8 transistor can package.

4. The photoacoustic gas sensor component of claim 1 where the infrared source is planar.

5. The photoacoustic gas sensor component of claim 1 where the wavelength selective bandpass filter is a selected from a class which includes at least a dielectric or a dichroic type IR filter.

6. The photoacoustic gas sensor component of claim 1 further comprising signal acquisition and signal processing circuitry formed integrated within the single hermetically sealed package.

7. The photoacoustic gas sensor component of claim 6 where the single hermetically sealed package includes a TO39 or TO8 transistor can package.

8. The photoacoustic gas sensor component of claim 6 where the infrared source is planar.

9. The photoacoustic gas sensor component of claim 6 where the wavelength selective bandpass filter is a selected from a class which includes at least a dielectric or a dichroic type IR filter.

10. An apparatus comprising:
a first housing which defines an internal sensing volume;
a second housing which includes at least an infrared source, and a microphone, where the infrared source and the microphone are integrated into the second housing as a single hermetically sealed package; and
an internal baffle within the second housing that prevents radiation from the infrared source from coupling directly to the microphone, where the second housing is carried at an open end of the first housing, wherein a first opening in the second housing provides a window through which infrared energy of a selected wavelength radiates from the infrared source into the internal sensing volume of the first housing and wherein the internal sensing volume is communicatively coupled to the microphone though a second opening in a face of the second housing.

11. An apparatus as in claim 10 where the second housing also includes signal acquisition and signal processing circuitry integrated into the single component package.

* * * * *